US006783645B2

(12) United States Patent
Cheng et al.

(10) Patent No.: US 6,783,645 B2
(45) Date of Patent: Aug. 31, 2004

(54) DISPOSABLE WORKING ELECTRODE FOR AN ELECTROCHEMICAL CELL

(75) Inventors: Jun Cheng, San Jose, CA (US); Petr Jandik, Los Gatos, CA (US); Nebojsa Avdalovic, Cupertino, CA (US)

(73) Assignee: Dionex Corporation, Sunnyvale, CA (US)

( * ) Notice: Subject to any disclaimer, the term of this patent is extended or adjusted under 35 U.S.C. 154(b) by 128 days.

(21) Appl. No.: 10/081,691

(22) Filed: Feb. 20, 2002

(65) Prior Publication Data

US 2003/0111340 A1 Jun. 19, 2003

Related U.S. Application Data

(60) Provisional application No. 60/342,137, filed on Dec. 18, 2001.

(51) Int. Cl.$^7$ .............................. C25B 9/02; C25B 9/06
(52) U.S. Cl. .................................................. 204/275.1
(58) Field of Search ...................... 204/275.1, 290.01, 204/290.03, 290.11, 290.12, 290.14

(56) References Cited

U.S. PATENT DOCUMENTS

| | | | | |
|---|---|---|---|---|
| 3,654,585 A | * | 4/1972 | Wickersham | ................. 439/65 |
| 4,640,289 A | * | 2/1987 | Craighead | ................... 600/391 |
| 4,710,403 A | | 12/1987 | Krause et al. | |
| 4,716,071 A | * | 12/1987 | Roberts et al. | ............. 428/209 |
| 4,938,860 A | * | 7/1990 | Wogoman | .............. 204/403.05 |
| 5,104,820 A | * | 4/1992 | Go, deceased et al. | ...... 438/109 |
| 5,324,322 A | | 6/1994 | Grill, Jr. et al. | |
| 5,437,999 A | | 8/1995 | Diebold et al. | |
| 5,521,425 A | * | 5/1996 | Deeney | ....................... 257/666 |
| 5,554,178 A | | 9/1996 | Dahl et al. | |
| 5,694,932 A | | 12/1997 | Michel et al. | |
| 5,989,409 A | | 11/1999 | Kurnik et al. | |
| 6,020,110 A | * | 2/2000 | Williams et al. | ............ 430/315 |
| 6,076,002 A | | 6/2000 | Cartmell et al. | |
| 6,110,354 A | | 8/2000 | Saban et al. | |
| 6,134,461 A | | 10/2000 | Say | |
| 6,258,229 B1 | | 7/2001 | Winarta et al. | |
| 6,276,054 B1 | | 8/2001 | Cartmell et al. | |
| 6,277,117 B1 | | 8/2001 | Tetzlaff et al. | |
| 6,287,451 B1 | | 9/2001 | Winarta et al. | |
| 6,291,053 B1 | | 9/2001 | Peiffer | |

FOREIGN PATENT DOCUMENTS

| | | | | |
|---|---|---|---|---|
| GB | 2 122354 A | * | 1/1984 | .......... G01N/27/46 |
| WO | WO 99/36786 A3 | | 7/1999 | |

OTHER PUBLICATIONS

Bagel et al., "Subfemtomolar Determination of Alkaline Phosphatase at a Disposable Screen–printed Electrode Modified with a Perflurosulfonated Ionomer Film", *Analytical Chemistry* 69:4688–4694 (1997).

Bozon, J.P.., "Development of Metal–Based Microelectrode Sensor Platform by Chemical Vapor Deposition", *Electroanalysis* 13:911–916 (2001).

(List continued on next page.)

*Primary Examiner*—Roy King
*Assistant Examiner*—Harry D. Wilkins, III
(74) *Attorney, Agent, or Firm*—Dorsey & Whitney LLP

(57) ABSTRACT

A flow-through electrochemical cell assembly with a disposable working electrode structure, including (a) a perimeter wall defining a sample flow channel including an inlet and an outlet, (b) a sample inlet line in fluid communication with the sample flow channel inlet, (c) a sample outlet line providing fluid communication between the sample flow channel outlet and a remote reference electrode, and (d) a disposable working electrode structure comprising an electrically conductive and electrochemically active working electrode region bound as a layer, directly or indirectly, to an electrically insulating substrate surface. The substrate surface is in fluid-sealing relationship with the sample flow channel, and the working electrode region is in fluid communication with said sample flow channel. The working electrode is vapor deposited, directly or indirectly, onto the organic polymer substrate through a mask, and a fluid seal is formed between said working electrode region and perimeter wall.

28 Claims, 3 Drawing Sheets

OTHER PUBLICATIONS

Lacourse, W.R., *Pulsed Electrochemical Detection in High–Performance Liquid Chromatography*, John Wiley, New York 1997, pp. 47–48 and 239–241.

Lindner, et al., "Microfabricated Potentionmetric Electrodes and Their In Vivo Applications", *Analytical Chemistry* 72:336A–345A (2000).

Madaras et al., Miniaturized Biosensors Employing Electropolymerized Permselective Films and their Use for Creatinine Assays in Human Serum, *Analytical Chemistry* 68:3832–3839 (1996).

Madou, M., *Fundamentals of Microfabrication*, CRC Press, New York 1997, p.60, 100.

Marzouk, et al., "A Conducting Salt–based Amperometric Biosensor for Measurement of Extracellular Lactate Accumulation in Ischemic Myocardium",*Analytical Chemistry* 69:2646–2652 (1997).

Soper et al., "Polymeric Microelectromechanical Systems", *Analytical Chemistry* 72:642A–651A (2000).

Henry, C.S., and Fritsch, I., "Microfabricated Recessed Microdisk Electrodes: Characterization in Static and Convective Solutions," *Anal Chem.* 71:550–556 (1999).

Mayer, M. and Ruzicka, J., "Flow Injection Based Renewable Eletrochemical Sensor Systems," *Anal. Chem.* 68:3808–3814 (1996).

Wang, "A Porous–Jet Flow–Through Electrode", Talanta, 1982, 29, 453–456.

Iwasaki, et. al. "Selective Electrochemical Detection using a Split Disk Array Electrode in a Thin–Layer Radical Flow System," Analytical Chemistry, 1996, 68 3797–3800.

Cosofret et al. "Microfabricated Sensor Arrays Sensitive to pH and K+ for Ionic Distribution Measurement in the Beating Heart," Analytical Chemistry, 1995, 67, 1647–1653.

Righezza et. al. "Optimization of the Design of a Thin–Layer Cell with a Single Electrode for Elecrochemical Detection in Liquid Chromatography," Analysis, 1992, 20, 333–340.

Cheng et. al. "Development and Characterization of Microfabricated Disposable Gold Working Electrodes for High–Performance Ion Chromatography and Integrated Pulsed Amperometric Detection," Analytical Chemistry, 2003, 75, 572–579/.

Cheng et. al. "Use of Disposable Gold Working Electrodes for Catlon Chromatography–Integrated Pulsed Amperometric Detection of Sulfur–Containing Amino Acids," Journal of Chromatography A, 2003, 997, 73–78.

Dionex Corporation, Mar. 1995, Revision 03 "ED40 Electrochemical Detector Operator's Manual".

William LaCourse: Pulsed Electrochemical Detection in HPLC, J. Wiley, 1997.

* cited by examiner

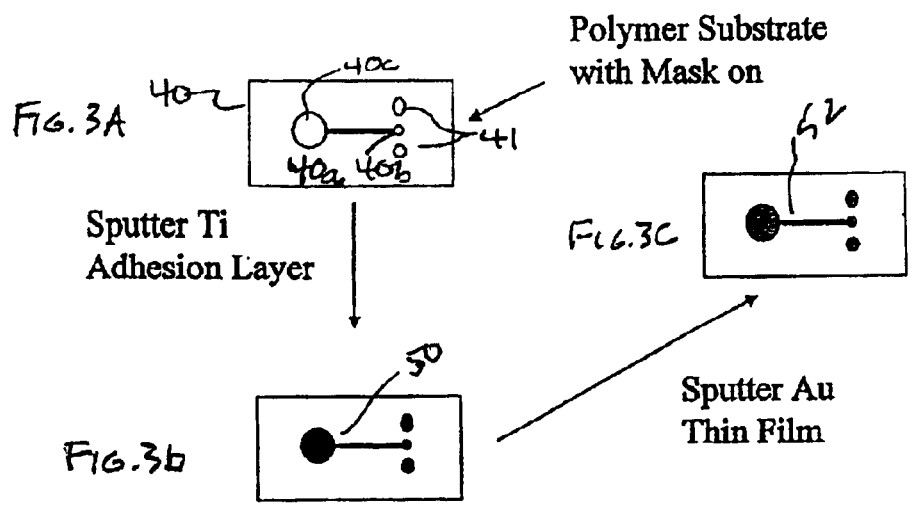

DISPOSABLE WORKING ELECTRODE FOR AN ELECTROCHEMICAL CELL

This application claims benefit of provisional application No. 60/342,137 filed on Dec. 18, 2001.

BACKGROUND OF THE INVENTION

Flow-through electrochemical cells are used as detectors for a variety of separation systems including chromatographic and ion chromatographic systems. Dionex Corporation sells such electrochemical cells under the trademarks ED40 and ED50 cells. Such cells include an amperometric working electrode in the form of a cylindrical wire embedded into a plastic block with the tip of the wire exposed to a sample flow-through channel, typically enclosed by a plastic gasket held in place under compression. These working electrodes are somewhat complicated and expensive to manufacture. After a period of use, the electrode must be replaced or reconditioned by laborious polishing or other methods which can lead to a lack of reproducibility of the detector output.

Thin film disposable electrodes have been used as in vitro test electrodes and as in vivo implantable monitoring electrodes in a variety of applications. See, for example, Michel, et al. U.S. Pat. No. 5,694,932; Dahl, et al. U.S. Pat. No. 5,554,178; Saban, et al. U.S. Pat. No. 6,110,354; Krause, et al. U.S. Pat. No. 4,710,403; Grill, Jr., et al. U.S. Pat. No. 5,324,322; Kurnik, et al. U.S. Pat. No. 5,989,409; Diebold, et al. U.S. Pat. No. 5,437,999; Kuennecke, et al. WO 99/36786; Bozon, et al., *Electroanalysis* 13:911–916 (2001); Soper, et al., *Analytical Chemistry* 72:642A–651A (2000); Lindner, et al., *Analytical Chemistry* 72:336A–345A (2000); Bagel, et al., *Analytical Chemistry* 69:4688–4694 (1997); Madaras, et al., *Analytical Chemistry* 68:3832–3839 (1996); and Marsouk, et al., *Analytical Chemistry* 69:2646–2652 (1997). However, none of the disposable electrodes described in these references are suggested for use in a flow-through electrochemical cell. Such cells have unique requirements such as the requirement of minimal contribution to peak broadening and reference potential being independent of sample composition.

The minimal contribution to peak broadening is predominantly determined by a low value of "chromatographic dead volume."

The independence of reference potential from solution composition is realized only in "true" reference electrodes e.g. calomel or Ag/AgCl equipped by a special type of electrolytic connection known as "salt bridge." A typical salt bridge is a cylindrical container filled with a 3 M KCl solution. The conductive connection to the reference half cell on one side and to the sample on the other side is realized using ion permeable diaphragms.

All existing microfabricated cells employ either "pseudo" reference electrodes (e.g. palladium) or reference half cells without salt bridges. The latter types of reference electrodes rely on a constant concentration of chloride ions in a measured sample. Achieving such constant concentration of chloride ions is not practical under chromatographic conditions.

There is a need to provide a disposable and readily removable amperometric working electrode for a flow-through electrochemical cell which is less expensive to construct and is replaceable, thus avoiding the potential lack of reproducibility incurred in reconditioning permanent working electrodes.

SUMMARY OF THE INVENTION

In one aspect of the present invention, a flow-through electrochemical cell assembly is provided with a disposable working electrode structure. The assembly includes (a) a perimeter wall defining a sample flow channel including an inlet and an outlet, (b) a sample inlet line in fluid communication with the sample flow channel inlet, (c) a sample outlet line providing fluid communication between the sample flow channel outlet and a remote reference electrode, and (d) a disposable working electrode structure comprising an electrically conductive and electrochemically active working electrode region bound as a layer, directly or indirectly, to an electrically insulating substrate surface. The substrate surface is in fluid-sealing relationship with the sample flow channel, and the working electrode region is in fluid communication with said sample flow channel. The working electrode structure is readily removable from said electrochemical cell assembly.

In another aspect of the invention, a method is provided for making a disposable electrode structure and sample flow channel for such an assembly. The method comprises the steps of (a) vapor depositing electrically conductive and electrochemically active material, directly or indirectly, onto an organic polymer substrate through a mask to form a pattern of a working electrode region, and (b) forming a fluid seal between said working electrode region and a perimeter wall to define a fluid sample flow channel with said working electrode region in direct fluid contact with said fluid sample flow channel.

BRIEF DESCRIPTION OF THE DRAWINGS

FIGS. 3a–3c are schematic representations of a method for masking a disposable electrode of the invention.

DETAILED DESCRIPTION OF THE PREFERRED EMBODIMENTS

Figure 1:
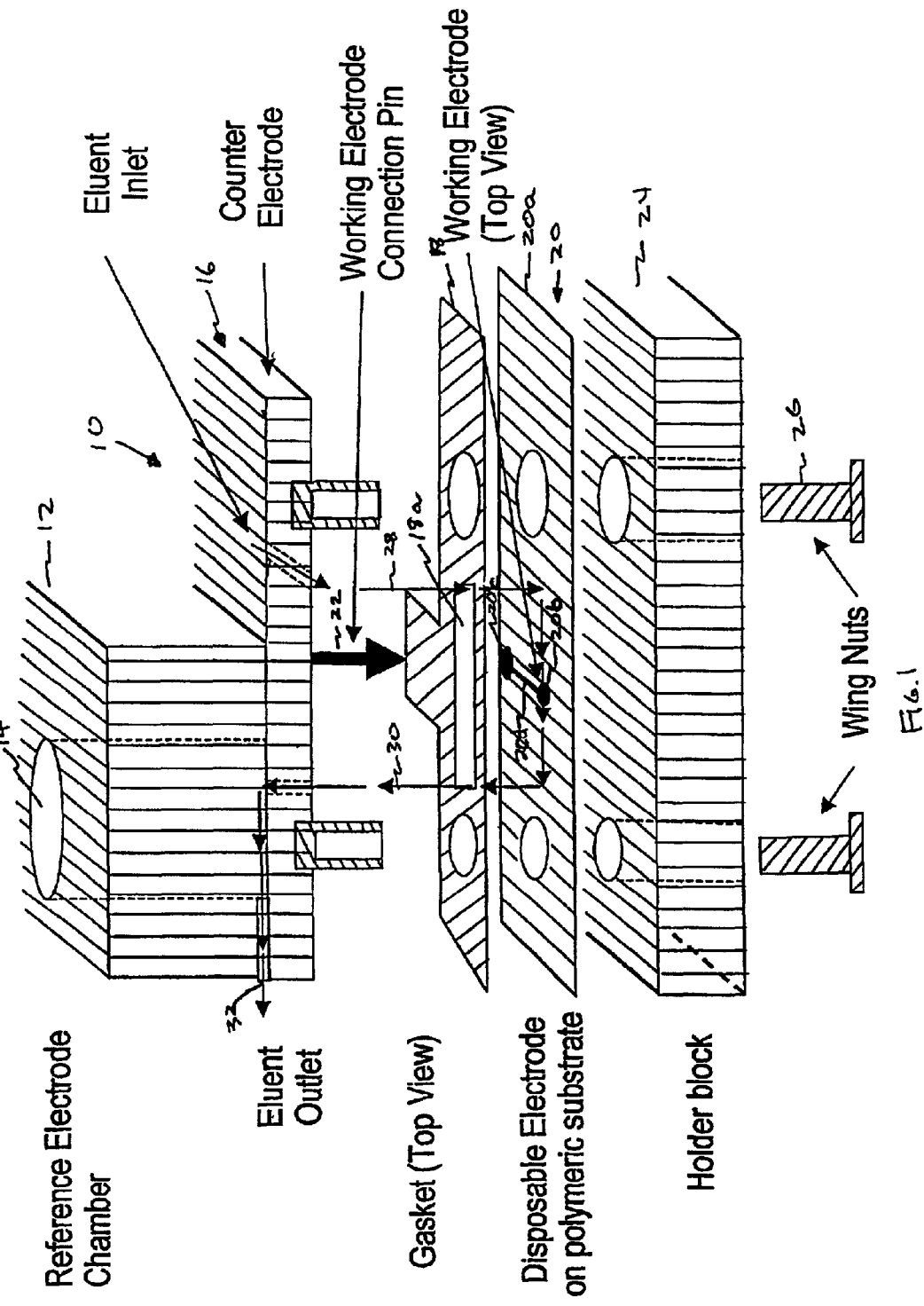
FIG. 1 is an exploded schematic view of an electrochemical cell assembly according to the invention including a disposable electrode.

Referring to FIG. 1, a flow-through electrochemical cell detector is illustrated including one embodiment of a disposable working electrode according the present invention. Most of the components of this cell can be similar to a conventional electrochemical cell such as the ED40 cell of Dionex Corporation, with the exception that the disposable working electrode structure replaces a generally permanent electrode structure which is periodically reconditioned as by polishing.

In general terms, the flow-through electrochemical cell includes a sample flow channel in contact with a working electrode. Sample analyte in a liquid eluent solution flows through the sample flow channel and from there through a reference electrode chamber. Electrode surface reactions are carried out on the working electrode, typically including an electrically conductive and electrochemically active material which is in direct contact with the sample solution flowing through the sample flow channel.

Specifically referring to FIG. 1, in one embodiment of an electrochemical cell assembly 10, a conventional reference electrode block 12 defines a contained cylindrical reference electrode chamber 14 through which the sample solution flows passing through the sample flow channel. Another suitable conventional electrode is in the form of a counter or auxiliary electrode 16.

The basic function of the auxiliary electrode is to prevent the electrical current from running through the reference electrode. This is achieved by means of so-called three-electrode potentiostats. See pages 47–48, 239–241, William R. LaCourse, *Pulsed Electrochemical Detection in High-Performance Liquid Chromatography,* John Wiley, New York 1997, pages 47–48 and 239–241.

If the passage of the current through the reference is not minimized, oxidation or reduction of the reference material can take place (e.g. AgCl reduced back to silver or Ag oxidized to silver oxide) or change of chloride concentration in the junction solution which may result in a poor constancy of the reference potential. The three-electrode potentiostats were introduced in the 1950s. Prior to that only two-electrode cells were in general use for voltammetry (i.e. measurement of current while controlling the potential)

As illustrated in FIG. 1, the sample flow channel in contact with the working electrode is defined by a gasket 18 which is retained in sealing relationship between the lower wall of counter electrode 16 and the upwardly facing wall of disposable working electrode structure 20 to be described hereinafter. Gasket 18 defines an interior cut-out forming a perimeter wall around sample flow channel 18a. The configuration of the sample flow channel 18a is defined by the thickness of gasket 18, and the length and width of the cut-out, preferably in the form of an elongated flow-through slot. As illustrated, the working electrode structure 20 includes a support substrate 20a, preferably formed of an organic polymer, and includes an electrically conductive and electrochemically active working electrode region 20b, preferable in the form of a thin layer, in a circular shape as illustrated. As will be described hereinafter, the working electrode region 20b is preferably formed by vapor deposition of an electrically conductive and electrochemically active material, directly or indirectly, onto substrate 20a. As used herein, "electrochemically active" means material suitable for facilitating the required electrochemical reactions for detection in electrochemical cells.

In the embodiment of FIG. 1, working electrode structure 20 also includes an electrically conductive contact region 20c, suitably also in the form of a circular disk, and an electrically conductive lead 20d interconnecting working electrode region 20b and contact region 20c. In a preferred embodiment, working electrode region 20b, contact region 20c and lead 20d are formed by vapor deposition of the same electrically conductive material directly or indirectly onto substrate 20a through a mask. As will be described hereinafter, an adhesion layer preferably is first deposited onto an organic substrate to facilitate binding of the electrode material. Preferably the adhesion material is of the same configuration as regions 20b and 20c and lead 20d and is also formed by vapor deposition through a mask of substantially the same shape. As in a conventional electrochemical cell, the assembly includes a working electrode connection 22, suitably spring loaded and in electrical communication at one end of a potentiostat, including a voltage or current source, and at the other end in electrical contact with region 20c to establish an electrical connection with working electrode region 20b through lead 20d.

As illustrated, the working electrode region 20b is disposed in the sample flow channel 18a in direct contact with sample flowing therethrough. In an illustrated embodiment, connection pin 22 and contact region 20c are disposed to the exterior of sample flow channel 18a out of fluid contact with liquid flowing through the flow channel. This has the advantage of simplicity. The working electrode, connector and contact pad are located in a planar arrangement on the same side of the polymeric substrate. This makes it possible to manufacture the entire working electrode in what is essentially a two-step deposition (e.g. with Ti and Au).

In contrast, the manufacturing of permanent electrodes requires many more steps: machining of a kel-F block, machining of a steel support plate, covering of a gold wire by a suitable insulating materials, machining of a Teflon ferrule for the liquid seal between the gold wire and the Kel F material, machining of the gold contact pad cylinder, insertion of the gold wire and of the contact pad into the opening in the Kel F material. Curing of the conductive polymer between the electrode wire and the contact pad cylinder. Sanding down the gold wire to the level of the Kel F material. Machine lapping of the gold wire, hand-polishing of the gold wire. Of these multiple steps, the hand polishing is very person-dependent and notorious for its lack of reproducibility.

The components are suitably held in the assembly under compression using a holder block 24 which maintains gasket 18 and electrode structure 20 in fluid sealing relationship. As illustrated, the compression is accomplished by the use of conventional wing nuts 26 or other clamping means. In one alternative form, not shown, gasket 18 can be formed integral with or adhered to substrate 20 as by an adhesive bond therebetween forming an integral unit which can be readily removed from the cell and replaced by another integral unit. Alternatively, gasket 18 can be mounted to counter electrode 16 or other support structure. In each of these or other possible configurations, a disposable electrode structure can be removed from the assembly and replaced alone or in combination with a gasket and support plate or holder block.

Gasket 18 typically is flexible with a thickness in the range of about 0.01 to 0.0005 inch consists of a fluoro polymer such as Teflon® or such polymeric materials as polyetherimide or nylon.

A similar type of gasket can be used as is used in the ED40 electrochemical cell. Such a gasket suitably includes an elongate slot for flow channel 18a, suitably 0.5 to 10.0 mm, preferably 0.8 to 5 mm long. The channel width is suitably 0.1 to 3 mm, preferably 0.5 to 1.5 mm. The gaskets are suitably 0.005 to 0.5 mm, preferably 0.013 to 0.1 mm thick.

As illustrated, the gasket can be held in place by bolts passing through openings in the gasket material at both ends of the gasket.

For use with disposable electrodes it is advantageous to modify the outer shape of the ED40 cell gasket as illustrated in FIG. 1. An elongated partial protrusion or tab covering the lead between the electrode and the contact pad improves the liquid seal. Also of advantage is to use thicker (>0.05 mm) and/or softer materials (PTFE) for gasketing of disposable electrodes.

In one embodiment, the gasket can also be made an integral part of the disposable electrode. The polymeric gasket can be permanently attached to the disposable electrode. This can be done either by oxygen plasma treatment of both surfaces followed by pressing the gasket against the electrode at room temperature. Alternatively, a permanent bonding of gaskets and electrodes can be achieved by using polyethylene coated polyester material of suitable thickness as a gasket. After cutting the material to the proper gasketing shape, the gasket is pressed to the face of the disposable electrode at a suitable elevated temperature, usually about 140° C.

Typically, the sample containing separated analytes in an eluent solution flows through conventional fittings, not shown, from a chromatographic separator, such as a packed bed chromatography column upstream of the electrochemical cell to flow channel 18a. The sample solution flows through inlet tubing connected to a sample flow channel inlet, not shown, in the path illustrated by arrows 28. As in the ED40 cell, the inlet can be formed by a pin hole opening through counter electrode 16 in the upstream end of flow channel 18a. The solution flows across flow channel 18a and exits through a sample flow channel outlet in the path illustrated schematically by arrows 30 and flows through a pin hole size opening, not shown, in counter electrode 16 into chamber 14 and exits chamber 14 through a fitting, not shown, through chamber outlet 32.

In another system, a conventional chemical or electrochemical suppressor is disposed between the electrochemical cell detector and the chromatography separator of an ion chromatography system.

The working electrode region is disposed within flow channel 18a to contact the flowing sample in eluent solution therein. A preferred way to accomplish this and to provide electrical contact with connector pin 22 is to space contact region 20c from working electrode region 20b and to interconnect them by lead 20d. This can be accomplished by the use of a mask which includes these three elements vapor deposited through the mask. In this configuration, the three elements are preferably in the form of thin film bound directly or indirectly to substrate 20a.

Figure 2:
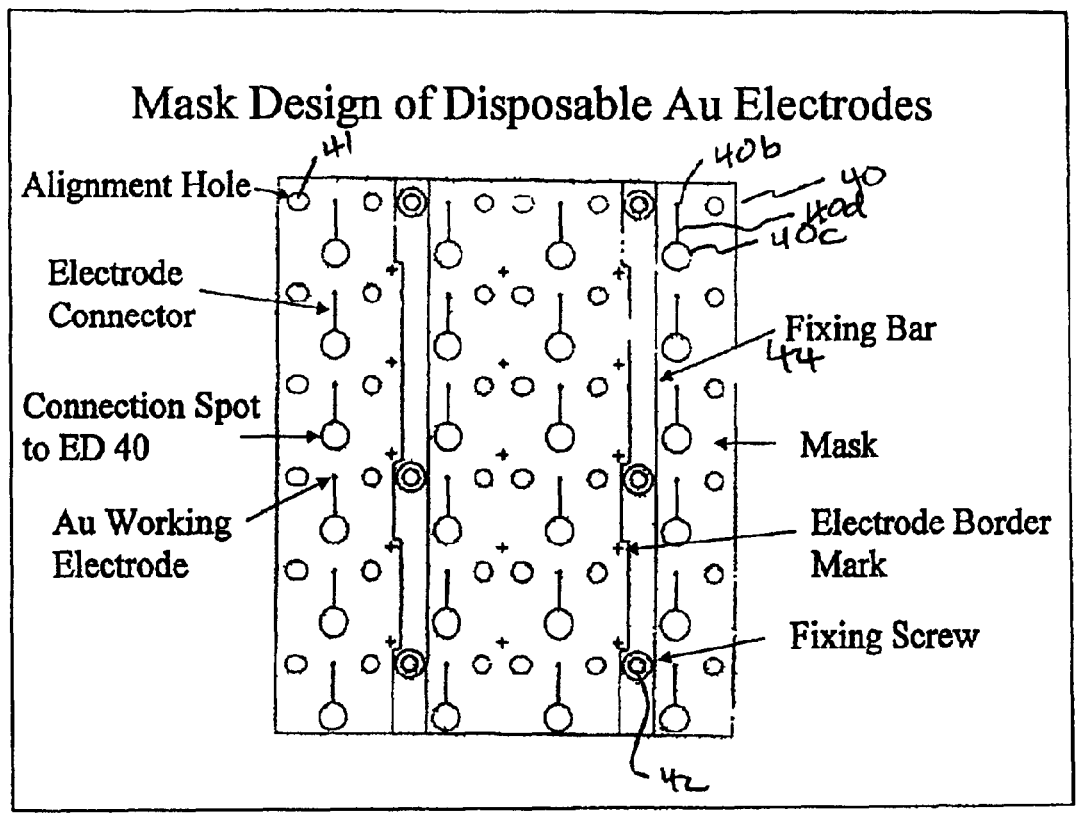
FIG. 2 is a top view of a masking for vapor deposition of the electrode onto a substrate.

Referring to FIG. 2, a top view of a mask 40 designed for vapor depositing multiple electrode region is illustrated. Mask includes alignment holes 41 to hold the screen in place and fixing screw 42 together with a fixing bar 44. In one embodiment, the mask 40 is prepared by wet etching of aluminum or stainless steel sheets. The electrical pattern is defined by openings in the mask. One way to vapor deposit the electrode region is by placing a sheet of polymeric substrate between mask 40 and a stainless steel plate, not shown. The mask includes working electrode opening 40b which defines working electrode region 20b, larger contact region 40c which defines contact region 20c and slot opening 40d which defines lead 20d. Suitable mask materials include metal (e.g. stainless steel, molybdenum), glass, quartz and silicon.

The metallic pattern may be prepared by conventional micro fabrication techniques used in semi-conduction manufacture as described, for example, in M. Madou, *Fundamentals of Microfabrication*, CRC Press, New York, 1997. These methods include but are not limited to physical vapor deposition (PVD) and chemical vapor deposition (CVD).

Preferably, before depositing the electrode region, an adhesion layer is deposited using the mask 40. This method is illustrated schematically in FIGS. 3a–c. Referring to FIG. 3a, a thin film of the adhesion layer 50, illustrated as the darkened region 50 in FIG. 3b, is sputtered through opening 40b, 40c, 40d and mask 40 as by sputtering using a high vacuum with Ar plasma. Such a technique is illustrated in M. Madou, Chapter 2, p. 60, FIG. 2.8 of *Fundamentals of Microfabrication* (CRC, 1997). Thereafter, as illustrated in FIG. 3c the mask is maintained in place. A suitable electrode material for direct contact with the sample in flow channel 18b is vapor deposited as a second thin film 52 onto a surface of the adhesion layer 50. The advantage of the adhesion layer is that it improves the cohesion between the electrode layer and the underlying substrate for any substrate, preferably an organic polymer material.

Suitably the adhesion layer is formed of a material such as titanium, tungsten, chromium and alloys of these materials. A titanium or tungsten titanium alloy adhesion layer is particularly effective to improve an adhesion of a metallic working electrode layer to the polymeric substrate. A typical thickness for the adhesion layer 50 is about 50 Å to 5,000 Å.

A suitable electrode material in region 20a is a metal, preferably a noble metal such as gold, platinum, copper or silver, or alloys thereof, although gold is the most frequently used one. In addition, a non-metallic electrode may be used for region 20b such as a carboneous material (e.g. glassy carbon, graphite or carbon paste) in combination with an adhesion layer such as titanium. Similar sputtering techniques would be employed. A typical thickness for the electrode material of layer 52 is about 100 Å to 10,000 Å.

A suitable top view configuration of working electrode region 20b is circular with a diameter of about 0.1 to 3 mm, and suitably about 0.5 to 2.0 mm, preferably about 1 mm. A suitable contact region 20c is larger because of the need to accommodate different types of useful contacting arrangements and to ensure good contact with pin 22.

Substrate 28 is preferably of a polymeric material with a thickness in the range of about 0.002 to 0.020 inches. It is preferably flexible for forming a good seal with gasket 18. Suitably, the polymeric material can be a polyester (such as polyethylene, terephthalate or polyethylene naphthalate), polycarbonate, polyolefin, polyimide or polyetherimide. Preferably, the polymeric material is a polyester (PEN or PET-type) or a polycarbonate.

Other alternative structures for the disposable working electrodes include different geometrical shapes of the working electrode area such as triangle, square or rectangle. Several possible arrangements relative to the flow path are possible for each of the non-circular geometries of the working electrodes. Also possible are comb-like patterns of two or more "finger" shaped electrodes connected to the same lead as the circular electrodes but protruding into the flow path either in a parallel or in radial fashion. Also feasible are intercalated electrodes or two comb-like electrode patterns protruding into the flow path from the opposing sides.

The electronics connecting the system can be the ones conventionally used in a Dionex ED40 or 50 electrochemical cell. A true reference electrode, e.g., Ag/AgCl wire immersed in a reference solution enclosed by suitable diaphragm or a glass membrane may be employed.

In one embodiment of the invention, microfabricated electrodes are used in conjunction with a salt bridge-equipped true reference electrode. The combination pH/Ag/AgCl electrode represents an improvement even over a "true" reference electrode. An integral part of the detection mechanism is a cyclical creation of a catalytic gold oxide layer on the working electrode's surface. The IPAD mode freshly creates and removes the amino acid-detection-enabling gold oxide layer with a frequency of 1 Hz or higher. The creation of gold oxide is pH dependent and in consequence different levels of oxidation current are generated as a detection background at different pH. With a Ag/AgCl reference electrode alone, any change of eluent pH, such as during a chromatographic mobile phase gradient, results in a strongly sloping chromatographic baseline. With the glass-membrane equipped true-reference electrode such as pH/Ag/AgCl the reference potential changes with pH in an identical fashion as the rate of gold oxide formation. The pH-connected change of the reference potential is thus providing an automatic compensation of the change of the oxidation current. The resulting baseline during a pH gradient is then completely flat.

In one embodiment of the invention, microfabricated electrodes are used with a pH compensated reference potential (i.e. true reference electrode, salt bridge, glass membrane).

The electrochemical cell of the present invention can be used in any application in which ED40 or ED50 cell is used. Thus, it can be used to detect separated amino acids, sugars, amino sugars, amines, amino thiols or the like. One of the advantages of the working electrode and reference electrode of the present invention is that they are capable of off-setting the change of pH and thus to eliminate excessive base line shifts. This is because of the built-in pH-related compensation of oxidation currents.

An important advantage of the disposable electrode is that it can be readily replaced after a single day or multiple day use at low expense before loss of performance of the cell.

The disposable electrodes of the present invention are compatible with a commercial low dead volume electrochemical cell. This enables use of a true reference or pH based reference potential.

A variety of samples were analyzed with different protocols using an electrochemical cell with a disposable electrode according to the present invention. The chromatograms from such experiments were very comparable to ones performed using the ED40 cell.

In order to more clearly illustrate the present invention, the following examples of its practice are presented.

Example 1

This illustrates a method for forming a sputtered thin film of titanium and gold on a polymeric substrate according to the invention.

1. Assembly of polymeric substrate, stainless steel base plate and stainless Steel masks for coating Polymeric film substrates obtained from Du Pont or GE were cleaned of all particles on their surface by blowing off with air, rinsed successively with water, alcohol and then dried in air. After punching the holes required for mounting the masks on top of the film, the polymeric substrates were put on top of a stainless steel base plate. We then placed first a thinner stainless steel mask and then a thicker stainless steel mask on the exposed side of the polymeric film. The patterns of the thinner mask is shown in FIG. 2. The thinner mask defines the shape of the electrode, connection lead and contact pad. The thicker mask, not shown, is used for keeping the thinner mask flat, completely co-planar and in close contact with the polymeric film. At the same time, the thicker mask has open cutout areas, thus providing the structural integrity without interference with the plasma during the sputtering of titanium and gold. The polymeric films are sandwiched tightly between the two masks and the supporting base plate. The whole assembly is being held together by bars and screws. The bars are positioned on top of the two masks.

2. Physical vapor deposition of titanium and gold

The polymeric substrates assembled with masks are placed in the sputtering chamber. A suitable vacuum is applied for 12 hours (overnight) to reach the vacuum required for sputtering (at least 40 mTorr). The water adsorbed inside the polymer is slowly removed from the chamber during that time. To initiate the deposition, the substrate remains enclosed in a low-pressure gas atmosphere (ca. 10 mTorr of argon). For RF plasma deposition the substrate is connected as anode and the metal source for deposition (target) is connected as cathode. A suitable RF frequency is within the range of 12–14 mHz. The suitable range of RF power is in the range of 1 to 2 kW. The deposition rate is different for different metals. For the same frequency and power of the RF field, titanium deposition is ca. 4.7 times slower than the deposition of gold (see for example Table 3.8, page 100, M. Madou, Fundamentals of Micromachining). The RF field generated between the substrate and target is the sole heating source during the metal deposition. The temperature of the polymeric substrate never exceeds the range of 50–70° C.

A titanium layer is sputtered first to promote adhesion of gold films to polymeric substrates. A typical thickness of the first metallic layer is 50 to 1000 Å. The layer of titanium is the only adhesion-promoting agent utilized in our process. There are no other adhesives being utilized to promote adhesion of gold layer to the polymeric substrate. The second layer (Au) is usually 100 to 5000 Å thick. The sputtering time varies from system to system because the coating rate depends on the power of the radio frequency (plasma source), the distance between the polymeric film and target (source of metal being deposited) and others.

Example 2

Assembling a Suitable Cell (1) Remove the ED40 cell body made of titanium from the stainless steel box serving as a Faraday Cage/electrode mounting container and unscrew the steel cylinder holder for the reference electrode.
(2) Verify that a black O ring (Viton) is in place in the lower part of the reference electrode chamber.
Insert a pH/Ag/AgCl reference electrode (glass cylinder) into the reference electrode chamber of the cell body.
(3) Install the steel cylinder holding the reference electrode in pre-defined position inside the reference electrode chamber.
(4) Connect the lead wires of the reference electrode to the "pH" and "Ag" pins of the pre-amplifier board.
(5) The white cable of the working electrode connection remains connected to the two "WE" pins.
(6) Unscrew the two winged screws and remove the permanent working electrode from the cell body.
(7) Remove the standard cell gasket and replace it by a cell gasket for use with disposable electrodes.
(8) Match the two holes of the disposable electrode unit (outside dimensions 2.5×3 cm) to the two posts protruding from the cell body. The two openings of the disposable electrode match the distance between the two posts (2 cm). Slide the disposable electrode all the way to the bottom of the two alignment posts. This positions the working electrode correctly inside the flow path defined by the gasket cutout. Make sure that the metallized side of the disposable electrode unit faces the electrode cell body and the gasket. The correct position of the working electrode can be verified through the transparent polyester substrate of the disposable electrode. The correct orientation of the disposable working electrode is indicated by the titanium color (not gold) being visible through the polyester when the unit is in the position close to the cell body.
(9) Slide the permanent electrode (or alternatively a less expensive holder block) onto the two posts pressing the disposable electrode against the cell body. Check visually the presence of the cell gasket and the correct contact between contact pin and contact pad.
(10) Mount the two winged nuts.
(11) Make liquid connections to and from the electrode cell.
(12) Slide the steel mounting box/Faraday Cage over the assembled cell.
(13) Connect the assembled cell to the electronic unit of the ED40 detector.

(14) Start the pump and wait until you see the first drops coming out of the outlet capillary.
(15) Check the pH readout on the screen of the ED40 electronic unit.
(16) Apply a suitable detection potential or detection waveform.

What is claimed is:

1. A flow-through electrochemical cell assembly comprising
   (a) a perimeter wall defining a sample flow channel including an inlet and an outlet,
   (b) a sample inlet line in fluid communication with said sample flow channel inlet,
   (c) a sample outlet line providing fluid communication between said sample flow channel outlet and a remote reference electrode, and
   (d) a disposable working electrode structure comprising an electrically conductive and electrochemically active working electrode region bound as a layer, directly or indirectly, to an electrically insulating substrate surface, said substrate surface being in fluid-sealing relationship with said sample flow channel, at least a portion of the substrate surface being exposed to the sample flow channel and said working electrode region being in fluid communication with said sample flow channel, said working electrode structure being removable from said electrochemical cell assembly.

2. The flow-through electrochemical cell assembly of claim 1 in which said working electrode structure further comprises an electrically conductive contact region bound as a layer, directly or indirectly, to said substrate surface and an electrically conductive lead providing an electric path between said working electrode region and said contact region, said contact region being bound to said substrate surface out of fluid contact with said sample flow channel.

3. The flow-through electrochemical cell assembly of claim 2 further comprising an electrically conductive connection pin having a first end in removable contact with said contact region and a second end adapted for electrical connection to a power source.

4. The flow-through electrochemical cell assembly of claim 1 in which said perimeter wall comprises a gasket forming a fluid-tight seal at the periphery of said sample flow channel.

5. The flow-through electrochemical cell assembly of claim 1 in which said working electrode region is exposed directly to said sample flow channel, without an intermediate layer.

6. The flow-through electrochemical cell assembly of claims 1 or 2 in which said working electrode region is between about 100 Å and 10,000 Å thick.

7. The flow-through electrochemical cell assembly of claim 1 in which said working electrode region is formed by vapor deposition of electrically conductive and electrochemically active material, directly or indirectly, onto said substrate.

8. The flow-through electrochemical cell assembly of claim 1 in which said substrate comprises an organic polymer.

9. The flow-through electrochemical cell assembly of claim 8 in which said organic polymer is selected from the group consisting of polyester, polycarbonate, polyolefin, polyimide and polyetherimide.

10. The flow-through electrochemical cell assembly of claim 1 in which said working electrode region comprises a metal or a carbonaceous material.

11. The flow-through electrochemical cell assembly of claim 1 in which said working electrode region is bound through an intermediate adhesion layer to said substrate.

12. The flow-through electrochemical cell assembly of claim 11 in which said adhesion layer is formed by vapor deposition onto said substrate.

13. The flow-through electrochemical cell assembly of claim 11 in which said adhesion layer is between about 50 Å and 5000 Å thick.

14. The flow-through electrochemical cell assembly of claim 11 in which said adhesion layer is formed of a material selected from the group consisting of titanium, tungsten, chromium, and alloys thereof.

15. The flow-through electrochemical cell of claim 1 in which said sample flow inlet is in fluid communication with a liquid chromatographic separator or flow injection analysis apparatus.

16. The flow-through electrochemical cell assembly of claim 1 wherein the active working electrode region has a diameter of about 0.1 to 3 mm.

17. The flow-through electrochemical cell assembly of claim 1 wherein the active working electrode region has a diameter of about 0.5 to 2 mm.

18. The flow-through electrochemical cell assembly of claim 1 wherein the active working electrode region has a diameter of about 1 mm.

19. A flow-through electrochemical cell assembly comprising:
   a working electrode structure including
      an electrically insulating substrate, and
      a working electrode disposed on a surface of the electrically insulating substrate;
   a sealing member positioned to define a sample flow channel bordered on at least one side by a region of the electrically insulating substrate selected such that the working electrode is positioned at least partially within the sample flow channel, the sample flow channel having an inlet and an outlet;
   a reference electrode in fluid communication with the sample flow channel; and
   a counter electrode in fluid communication with the sample flow channel.

20. A flow-through electrochemical cell assembly according to claim 19, further comprising:
   a clamp compressing the sealing member between the working electrode structure and the counter electrode, such that the counter electrode defines at least one side of the sample flow channel.

21. A flow-through electrochemical cell assembly according to claim 20 wherein the clamp is releasable to allow for removal of the working electrode structure from the flow-through electrochemical cell assembly.

22. A flow-through electrochemical cell assembly according to claim 19, wherein the reference electrode is equipped with a salt bridge.

23. A flow-through electrochemical cell assembly according to claim 19, the working electrode comprising a pH/Ag/AgCl electrode.

24. A flow-through electrochemical cell assembly according to claim 19, wherein the working electrode is microfabricated.

25. A flow-through electrochemical cell assembly according to claim 19, wherein the working electrode comprises an electrically conductive material and an electrochemically active material.

26. A flow-through electrochemical cell assembly according to claim 19 wherein the working electrode has a diameter of about 0.1 to 3 mm.

27. A flow-through electrochemical cell assembly according to claim 19 wherein the working electrode is affixed to the insulating substrate with an adhesion material.

28. A flow-through electrochemical cell assembly comprising:

a reference electrode including a wall having an inlet and outlet spaced therefrom;

a sealing member mounted to said wall and defining a sample flow channel fluidly coupling said inlet and said outlet; and a working electrode structure including an electrically insulating substrate and a working electrode disposed along a surface portion of said electrically insulating substrate;

wherein said sample flow channel is capped by said working electrode structure such that said working electrode is in fluid communication with said sample flow channel.

* * * * *

UNITED STATES PATENT AND TRADEMARK OFFICE
CERTIFICATE OF CORRECTION

PATENT NO. : 6,783,645 B2
DATED : August 31, 2004
INVENTOR(S) : Jun Cheng et al.

It is certified that error appears in the above-identified patent and that said Letters Patent is hereby corrected as shown below:

Column 10,
Line 33, change "surface of" to -- surface portion of --.

Signed and Sealed this

Fifth Day of April, 2005

JON W. DUDAS
*Director of the United States Patent and Trademark Office*